(12) United States Patent
McCraw (10) Patent No.: US 7,182,758 B2
(45) Date of Patent: Feb. 27, 2007

(54) APPARATUS AND METHOD FOR DRAINAGE

(76) Inventor: John B. McCraw, 4280 Quail Run Rd., Jackson, MS (US) 39211

( * ) Notice: Subject to any disclaimer, the term of this patent is extended or adjusted under 35 U.S.C. 154(b) by 287 days.

(21) Appl. No.: 10/715,549

(22) Filed: Nov. 17, 2003

(65) Prior Publication Data
US 2005/0107756 A1 May 19, 2005

(51) Int. Cl.
- A61M 1/00 (2006.01)
- A61M 5/00 (2006.01)
- A61M 5/32 (2006.01)
- A61F 13/00 (2006.01)

(52) U.S. Cl. .................... 604/541; 604/264; 604/265; 604/266; 604/305; 604/307; 604/316; 604/317; 604/543

(58) Field of Classification Search ........ 604/264–266, 604/305, 307
See application file for complete search history.

(56) References Cited

U.S. PATENT DOCUMENTS

| | | | |
|---|---|---|---|
| 5,358,492 A * | 10/1994 | Feibus ........................ | 604/264 |
| 6,135,116 A | 10/2000 | Vogel et al. | |
| 6,605,068 B2 * | 8/2003 | Righetti ....................... | 604/264 |
| 6,929,626 B2 * | 8/2005 | DiCarlo et al. ............. | 604/249 |

* cited by examiner

Primary Examiner—Tatyana Zalukaeva
Assistant Examiner—Melanie J. Hand
(74) Attorney, Agent, or Firm—Aaron Passman (57) ABSTRACT

An apparatus for drainage of a wound or surgical site of a human or animal fits anatomically, passes from inside the wound or surgical site percutaneously or covering an open wound surface and extends externally for accumulation of fluids. A plurality of fibers each with an internal end, middle and an external end is elongate with a thickness and a length wherein its thickness is substantially less than its length for flexibility. The fibers form a loose bundle with gathered external ends and with internal ends unrestrained for spreading divergently inside the wound or surgical site. A collector is positioned in fluid communication with the gathered external ends for accumulating bodily fluid guided along and amongst the fibers from the internal ends along the middle and to the external ends during drainage. Vacuum connects to draw fluid from the collector. A method has steps of providing fibers with the internal ends unrestrained, the external ends gathered in a collector to accumulate drained fluid. The method guides bodily fluid along and amongst the fibers from the internal ends along the middle and to the gathered together external ends during drainage. The fibers spread divergently for accumulating bodily fluid inside the wound or surgical site. A method of manufacture of the apparatus has the steps of accumulating a plurality of fibers with internal ends, a middle and external ends in a loose bundle but gathering together in a collector at their external ends while leaving the internal ends unrestrained.

22 Claims, 9 Drawing Sheets

APPARATUS AND METHOD FOR DRAINAGE

CROSS-REFERENCE TO RELATED APPLICATIONS

None.

STATEMENT REGARDING FEDERALLY SPONSORED RESEARCH

Not applicable.

SEQUENCE LISTING

Not applicable.

BACKGROUND OF THE INVENTION

The purpose of a drain is to evacuate fluid or gas that is present or likely to accumulate in a localized cavity. Typically, drains are used in an abscess cavity, to treat pneumothorax, or evacuation of blood, serum or lymph from a wound. Drains also remove pus or transudate or alternately to irrigate cavities. The process of drainage eliminates the dead space in a cavity. Herein and throughout this disclosure the cavity will be referred to as the wound or surgical site no matter what the reason for the cavity to be drained. Drainage systems are closed if they capture the fluids with tubing coupled to a closed container or canister and are open if fluid is accumulated in gauze or corrugated rubber sheet. Canisters and collapsible vessels use vacuum or the restoration force of the collapsed vessel to provide respectively, active high or low drainage pressure. Completely passive drains operate on the pressure differential between the inside and outside of the body.

Porex of Newnan, Ga. makes bulb drains and so does Chimed (Via dell'Artigianato, 49 57121 Livorno, Italy that also makes bellows drains; all those are relatively low pressure drains. Chimed also sells a Drenomax high vacuum canister to actively apply vacuum to the drain tubing. Alternatively there is a Drenomax passive drain bag that merely uses pressure differential to accumulate the fluid flow from the drain tube without any vacuum. Chimed also sells Drenomed S-line and R-line drains that are extruded medical grade silicone structure with longitudinal ducts open to the body cavity for passing fluid and the open channels are for resisting clogging. Those semi-rigid structures resist kinking and tissue in-growth. Ethicon a part of Johnson & Johnson sells Blake round and flat extruded structures that are similar in construction and purpose to the R-line and S-line drains. These drains are essentially open ducts within the body cavity and enter a hub connected to the collection vessel or container so that the fluid may be captured as it leaves the body. Degania Silicone of Cumberland, R.I. makes canisters, perforated tubes and bulbs. Jackson-Pratt makes a drainage bulb with a tube to place into the surgical area; again the collapsed bulb draws the fluid from the surgical area and can be emptied and reused. A drain for a wound or surgical site is needed that is less intrusive, is removed easily, is more effective, remains flexible and is capable of guiding fluid flow from the body without kinking or creasing so that healing accelerates and trauma is minimized. Typical tubular drains are placed in the patient after surgery to allow fluids that accumulate in the wound or surgical site after surgery to pass from within in the body to a capture container for analysis and then disposal. Drainage is essential to removing detritus caused by and generated during surgery and healing. The quicker drainage takes place, the faster healing proceeds and the patient recovers.

The human body responds to surgical intrusion initiating healing with white cells, swelling and bleeding. That healing response results in an automatic bodily clean up of the wound or surgical site. Healthy patients heal quickly as a result of the automatic healing response and good drainage accelerates that process. Removal of detritus promotes prompt recovery. Closure of the surgery typically includes a drain tube to allow the results of clean up to leave the body.

Recent U.S. Pat. No. 6,605,068 includes a gravity drainage cord formed by braiding a plurality of strands of silk of the type used for surgical sutures, and fitted or assembled loosely, in the median region, in a tubular sheath made of a material such as silicone. The outer silicone tube facilitates sliding of the assembly with respect to tissue, increases biocompatibility and allows optional coupling to mechanical aspiration units. Capillary action is said to be the mechanism of drainage. The protrusion of the cord into the wound allows small movement and if more than one cord is used some distributing and spreading are taught to increase drainage. Inside the cavity to be drained the tube may have radial holes to facilitate drainage. No use of the cords without the tube is acceptable and no mechanism other than capillary action is disclosed. The disclosure of U.S. Pat. No. 6,605,068 is incorporated by reference and made a part of this background.

The therapeutic effect of promoting drainage from wound cavities is known and has been the subject of devices to promote drainage have come in many forms, but may be classified generally in three groups. The first general group, have a hollow structure, such as a tube, which is placed in the wound to allow the removal of wound discharge by, e.g., capillary action and/or siphoning and/or gravity. A number of these "tube" type drains have also been used in conjunction with vacuum producing apparatus to actively assist drainage. Advantages shared by tube-type surgical drains are ease of insertion into a wound cavity and the volume of discharge does not generally affect their drainage function. As they provide constant drainage, the need to replace them is reduced. There are a number of disadvantages of tubular surgical drains including the difficulties of avoiding infection and promoting healing inherent in a device inserted in a wound cavity. Tubular surgical drains tend to be prone to blockage and other forms of obstruction, e.g., when the tube opening contacts body tissue the passage of discharge may be plugged or obstructed.

The second general group, of surgical drain devices, include those made of various forms of fibers and fabrics having absorptive properties, that are placed in a wound cavity to allow removal of wound discharges, e.g., by absorption. Advantages shared by these "fabric" type surgical drains are that they can be sized relatively easily and manipulated regardless of the size of the wound cavity and they are less prone to blockage or obstruction than tube-type drains. As with tube-type drains, fabric drains suffer from a number of disadvantages, such as susceptibility to sloughing or fragmentation, which may promote irritation and associated infection, and their drainage capacity maybe limited to the fluid retention capacity of the fabric, i.e., the drainage is not continuous. Using hydrophilic fibers, e.g., cellulose derived and yarns may aggravate flow problems, due to their water binding properties. A consequence of the drainage capacity limitation is that fabric-type surgical drains must ordinarily be replaced on relatively short intervals.

U.S. Pat. No. 6,135,116 has an active drainage system with positive and negative pressure applied to a wound dressing applied to a foot ulcer by a foot wrap. The use of vacuum applied to gauze is thus taught. U.S. Pat. No. 6,135,116 is incorporated by reference and made a part of this background.

Conventional fabric-type drain materials are often so loosely woven that they fragment which increases the risk of infection. Moreover, natural fibers like cotton, and other cellulose, are themselves prone to sloughing or fragmentation that also increase the risk of infection. In addition, depending on the fibers selected, known fabric-type surgical drains may decompose over time, again necessitating more frequent replacement, and irritating of the wound cavity. Another limitation of known fabric-type surgical drains is that, once positioned, they may be difficult to relocate or retrieve.

The third general group, of surgical drain devices, is a hybrid of the described tubular and fabric drains including both a hollow structure and absorptive fibers. In these combination surgical drains, a fabric is usually either wrapped around or arranged within a hollow structure to form a composite to insert into a wound. Combination drains enjoy some of the advantageous properties of both tube and fabric-type drains. While this type of drain has the advantage of ease of manipulation and may have better drainage characteristics than the other general types of surgical drains, it may also suffer from their disadvantages. An example of a combination-type drain routinely used in surgical procedures, is made from gauze, e.g., a loosely woven cotton fabric, which may be layered and cut to size and then placed in either surgical sheathing or a tubular part cut from a rubber glove prior to insertion into a wound cavity. The surgical sheathing or rubber glove part is used to help prevent loose fragments or threads of the gauze from entering the wound cavity. Gauze is prone to fragmenting leaving many loose threads when it is cut and additional parts of the fabric may fall away under minimal pressure in the form of lint. The use of the sheath or glove to contain lint is not completely effective or convenient for use in an operating room setting. Furthermore, drainage with this type of surgical drain may be limited to the fluid retention capacity of the fabric and evaporation. Typical of this is FIG. 9 in U.S. Pat. No. 5,358,492 with absorbent filler cord within the surrounding woven warps and wefts forming tube like channels. U.S. Pat. No. 5,358,492 is incorporated by reference and made a part of this background.

Other known surgical drains, include 'cigarette drains', made by surrounding a strip of gauze with a protective covering of rubber, gutta-percha, or the like; and drains formed by pushing a single layer of gauze into a wound cavity, the layer of gauze being packed with several thick wicks of gauze as it is pushed into the cavity. As with other known surgical drains, these drains have lint and their drainage capacity may be limited to the fluid retention capacity of the fabric.

Often a vacuum may be applied to the external end of the tubular drain to aid in removal of detritus. The vacuum will tend to overcome clogging of the fluids drawn through the drainage tube. Specifically, the drainage detritus include fluids with tissue, blood and other cellular matter. Thus the drainage fluids are often quite thick or viscous and adhering to the inside of the tubular drain restricting flow or even coagulating forming a restriction therein notwithstanding vacuum application.

Another problem encountered with the using of tubular drains is that drainage is localized about the internal end of the tube particularly when vacuum is applied externally. Localization of drainage is not effective to remove the detritus and accelerate healing of the wound or surgical site. Drainage is drawn primarily from the area adjacent to the internal end; thus, fluid is drawn mostly there from and not through out the wound or surgical site. Moreover, the vacuum applied to the drain tube can draw the adjacent internal tissue into the internal end resulting in restriction of flow and perhaps collapse of the tubular passageway stopping drainage and requiring withdrawal and removal and replacement of the drain tube. Additional trauma to the wound or surgical opening and interference with the healing process are detrimental and undesired consequences. To prevent collapse of the tubular passageway drain tubes are made with a thick wall to resist the high vacuum necessary to draw the detritus out of the wound or surgical site. Increased vacuum promotes restriction caused by internal tissue drawn into the end of the drain tube.

Yet another difficulty with tubular drains is their relatively rigid circular cross section. In particular, the incision made through the skin to enter the body is often linear or a puncture and thus not circular. When the wound or surgical opening through the skin is cut by a scalpel, torn by puncture or is an injury, it has a rough edge. Typically, the tubular drain placed in a surgical opening is sutured to the patients skin to maintain its position. If suturing is performed to secure the tube, it pulls and is uncomfortable during drainage and removable.

A better drain is needed to anatomically fit percutaneously into or through the wound or surgical opening and draw fluid from inside the wound or surgical site. Guiding fluid from inside the wound or surgical site and resisting clogging, impediment and localization would be welcome during external removal of accumulated detritus. An improved drainage apparatus and methods of use and manufacture that can take the place of a tubular drain to accelerate wound or surgical site clean up and healing would be of value and aid healing.

SUMMARY OF THE INVENTION

An apparatus for drainage of a wound or surgical site of a human or animal fits anatomically and passes from inside the wound or surgical site through the wound or surgical opening extending percutaneously externally for accumulation and removal of fluids. The apparatus for drainage preferably has a plurality of fibers each flexible and having an internal end, an external end and between them a middle. It is desired that each fiber is elongate with a thickness and a length so the fiber thickness is substantially less than its length for flexibility. The plurality of fibers forms preferably a loose bundle having gathered together external ends leaving internal ends unrestrained for spreading divergently inside the wound or surgical site. As will be explained herein the middle being a loose bundle allows fiber shifting and guidance of fluid flow out of the wound or surgical site while minimizing restriction of flow.

A collector is preferably positioned in fluid communication with the gathered together external ends of the loose bundle of the plurality of fibers. The collector preferably accumulates bodily fluid guided along and amongst the fibers from the internal ends along the middle and to the gathered together external ends during drainage of fluid from inside the wound or surgical site. The plurality of fibers at their unrestrained internal ends desirably spreads divergently about the inside wound or surgical site for guiding fluid. A source of vacuum in an active system connects to draw fluid from the collector that is positioned in fluid communication with the gathered together external ends. The plurality of fibers in the preferred embodiment are each a filament, for example, Nylon suture but they may be selected from the group of structures consisting essentially of monofilaments, strings, strands, hollow fibers or any combination thereof. The plurality of fibers may be made from a biocompatible material selected from the group consisting essentially of polymers, cellulose, natural substances or any combination thereof. The biocompatible material can be bio-absorbable but must maintain its structure over the at least the period during which the drainage is desired. The plurality of fibers may include an anticoagulant for resisting the clotting of fluid passing there about, along and among. Anticoagulants such as heparin, saline solution or even water adhered to absorbed in or about the loose bundle of the plurality of fibers may be provided to minimize the fluid coagulation or clotting on or to the fibers increasing the time over which fluid may easily drain. The plurality of fibers may include an anti-microbial for deterring the passing of microbes there about, along and among. The source of vacuum if not regulated may have a regulator connected between it and the collector for adjusting the amount of vacuum applied to the gathered together external ends.

A method for drainage of a surgical site of a human or animal uses the apparatus and includes steps of providing a plurality of fibers each having an internal end, an external end and there between a middle. Each fiber is elongate with a thickness and a length wherein its thickness is substantially less than its length for flexibility. The plurality of fibers is gathered together near their external ends. Exactly how the external ends are gathered together is not important to the method of drainage so long as the fluid flow may pass along the plurality of fibers and be accumulated. The step of allowing the internal ends to remain unrestrained is preferably performed. Accumulating fluid in a collector positioned in fluid communication with the gathered together external ends is a fluid drainage step. The step of guiding bodily fluid about, along and amongst the fibers from the internal ends along the middle and to the gathered together external ends during drainage of fluid from a wound or surgical site is preferred. The plurality of fibers at their unrestrained internal ends are inside the wound or surgical site for the preferred steps of spreading divergently for accumulating bodily fluid and for guiding bodily fluid about, along and amongst the fibers from the internal ends along the middle and to the gathered together external ends during drainage.

The method has the steps of connecting a source of vacuum and drawing fluid from the collector positioned in fluid communication with the gathered together external ends. It is preferred that the fibers be selected from the group consisting essentially of flexible filaments, strings, strands, hollow fibers or any combination thereof and/or the fibers be made from a biocompatible material selected from the group consisting essentially of polymers, cellulose, natural substances or any combination thereof. The step of using biocompatible material being bio-absorbable over time is desired. The step of including an anticoagulant for resisting the clotting of fluid passing along the plurality of fibers is valuable as is the step of including an anti-microbial such as silver compounds, bactericides, etc. for deterring the passing of microbes along the plurality of fibers. The step of adjusting the source of vacuum with a regulator connected between the source of vacuum and the collector is desired. The step of introducing the plurality of fibers with the steps of constraining the internal ends and the middle with an introducer, removing the introducer while leaving the plurality of fibers inside the wound or surgical site is preferred so the step of spreading divergently the internal ends results inside the wound or surgical site. The step of allowing the plurality of fibers in the middle to shift relative to one another is preferred so that the cross section the loose bundle approximates the cross section of the wound or surgical opening, for example, a percutaneous incision through which the middle passes for guiding drainage during healing.

A method of manufacture of an apparatus for drainage of a wound or surgical site of a human or animal that fits anatomically and passes from inside the wound or surgical site percutaneously and extends externally for accumulation of fluids may have the steps of accumulating and orienting a plurality of fibers each with an internal end, an external end and a middle there between in a loose bundle and gathering at their external ends each fiber elongate with a thickness substantially less than its length for flexibility while leaving the internal ends unrestrained. It is preferred to position a collector in fluid communication with the gathered together external ends for accumulating bodily fluid guided along and amongst the fibers from the internal ends along the middle and to the gathered together external ends during drainage of fluid from inside the wound or surgical site.

DETAILED DESCRIPTION

Figure 1:
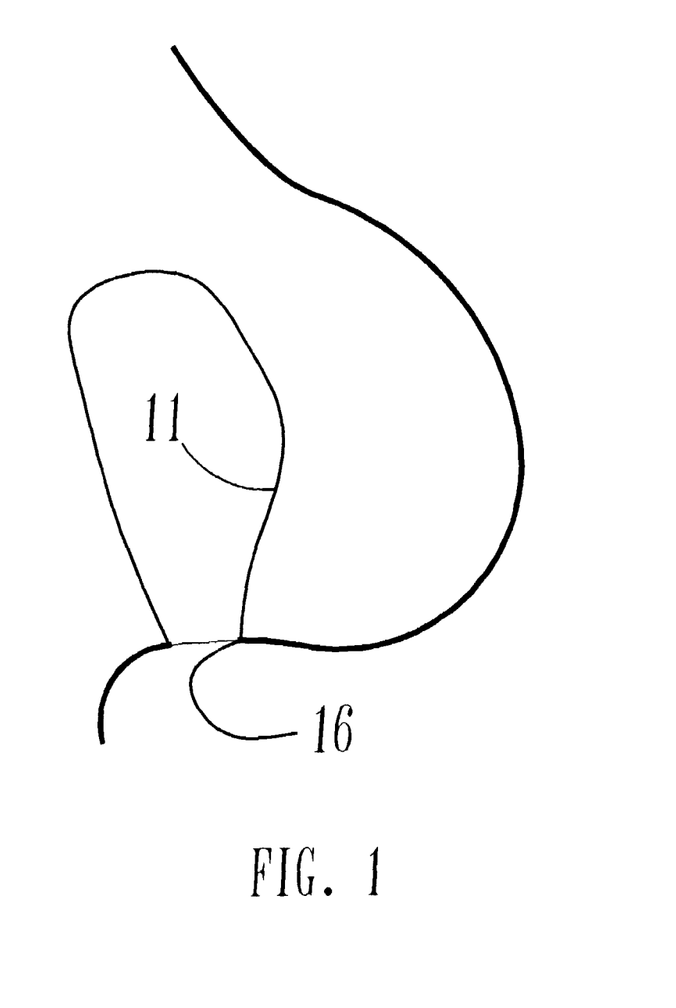
FIG. 1 is a side view in cross section of a wound or surgical site for receiving an apparatus for drainage.
Figure 2:
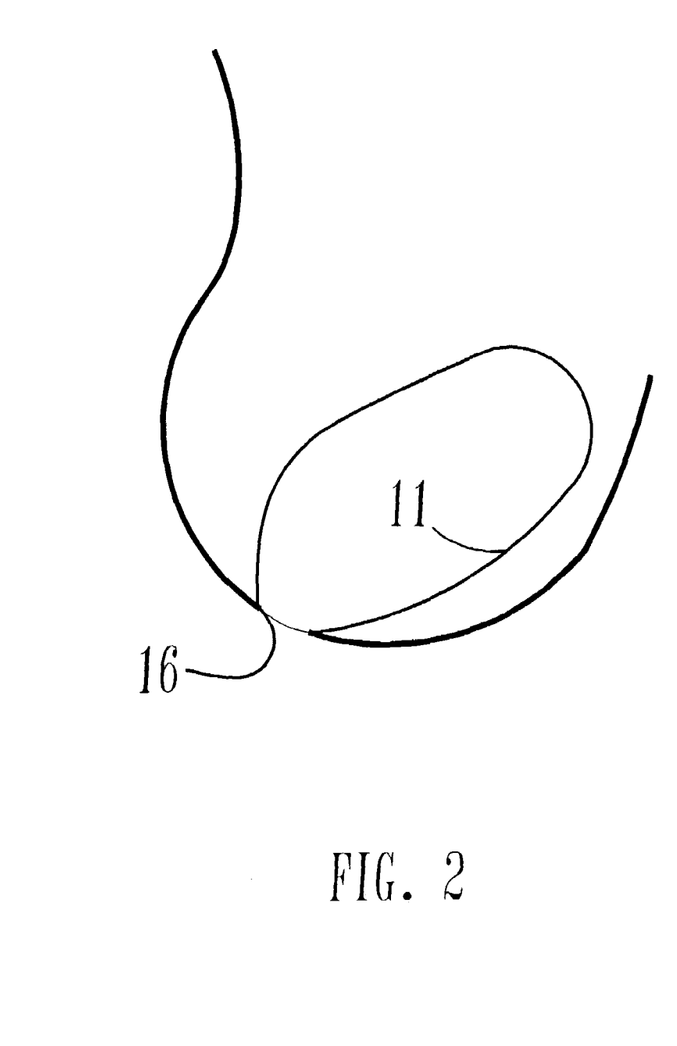
FIG. 2 is a front view in cross section of the wound or surgical site for receiving the apparatus for drainage.
Figure 3:
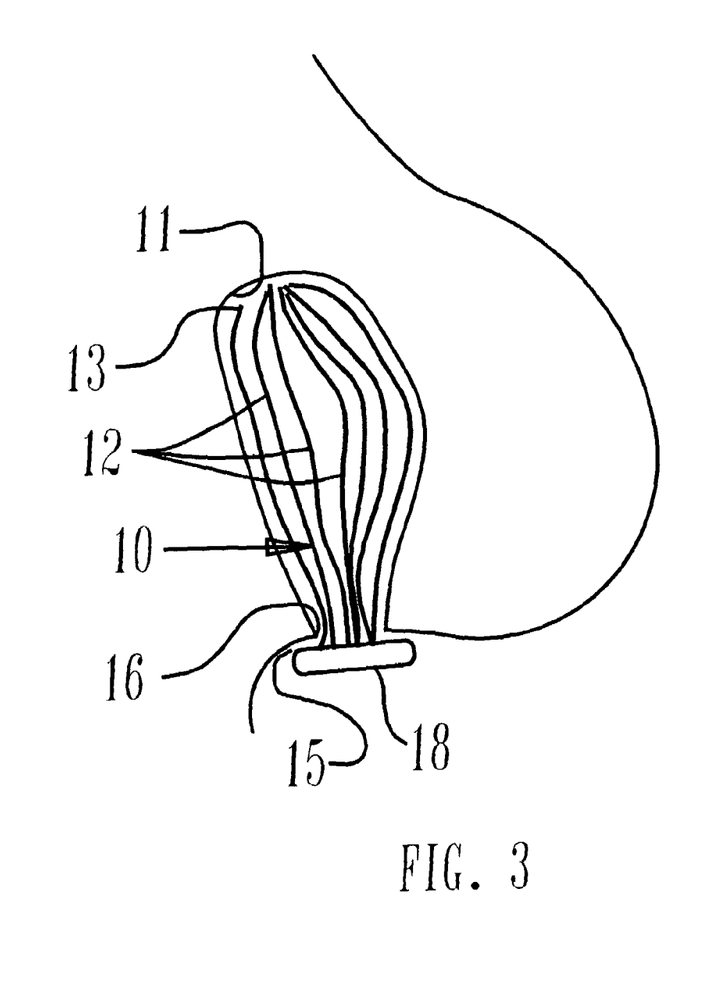
FIG. 3 is a side view of the apparatus for drainage placed in the wound or surgical site of FIG. 1 and wherein the internal ends of the loose bundle of fibers have spread out inside the wound or surgical site to accumulate and guide fluid there from during drainage.
Figure 4:
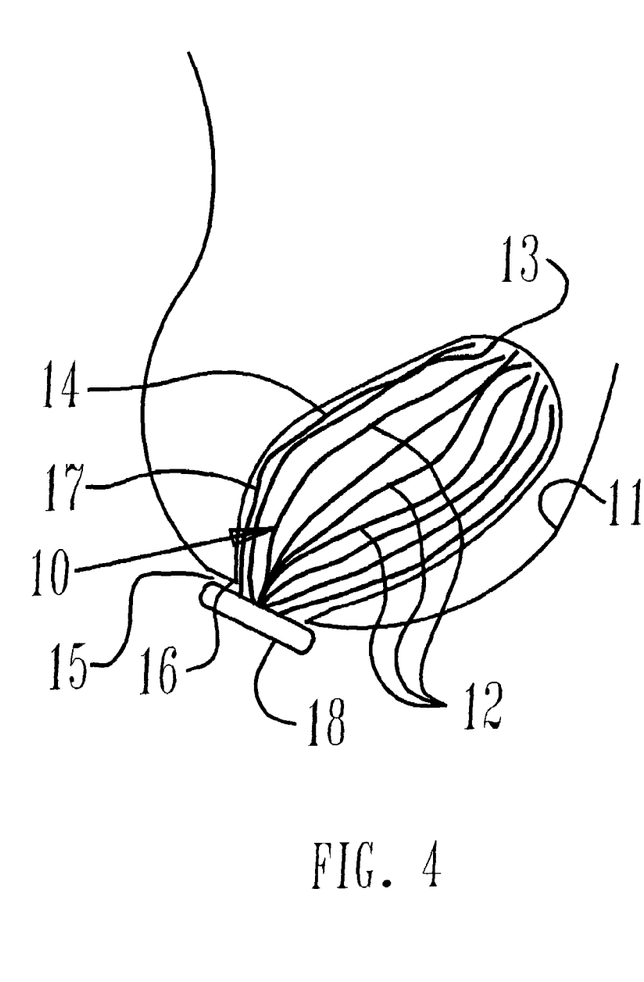
FIG. 4 is a front view of the apparatus for drainage placed in the wound or surgical site of FIG. 2 and wherein the internal ends of the loose bundle of fibers have spread out inside the wound or surgical site to accumulate and guide fluid there from during drainage.

An apparatus for drainage 10 of a wound or surgical site 11 accommodates a wound or surgical site 11 anatomically, passes from inside the wound or surgical site 11 percutaneously and extends externally for accumulation of fluids, see FIGS. 1 to 4. The apparatus for drainage 10 has a plurality of fibers 12 and each is elongate and has an internal end 13, middle 14 and an external end 15. It is desired that each elongate fiber 12 be of a thickness about 0.5 to 2 mm and a length perhaps 4 to 8 cm so its thickness is substantially less than its length for flexibility. Preferably each fiber 12 is medical grade suture material e.g., Nylon and is long enough to extend from inside the wound or surgical site 11 through a wound or surgical opening 16 to the external accumulation of the surgical fluids, as depicted in FIGS. 3 and 4. The plurality of fibers 12 form a loose bundle 17 having gathered together external ends 15 and with internal ends 13 unrestrained for spreading divergently inside wound or surgical site 11, shown in FIGS. 3, 4, 9, 10, 11, 12 and 14. Although not limiting, loose bundle 17 has about eight to twelve generally equal lengths of suture, for example, that have been found to accommodate the needs of the apparatus for drainage 10 and are able to guide fluids from inside wound or surgical site 11 for transport through wound or surgical opening 16.

The plurality of fibers 12 are preferably Nylon suture but may also be selected from the group consisting essentially of filaments, strings, strands, hollow fibers or any combination thereof. Wicking and tubular materials are not specifically mentioned as possible fibers 12 as the problems noted in the background relative to prior drains remain with the uses of those absorbent materials. Capillary attraction may not be the primary mechanism of drainage and thus, filaments are preferred for the plurality of fibers 12. Although Nylon material has an affinity for water, that mechanism is helpful but not the sole principle upon which the apparatus for drainage 10 operates. Biocompatible material selected from the group consisting essentially of polymers, cellulose, natural substances or any combination thereof can be used as the material in the plurality of fibers 12. The biocompatible material may be bio-absorbable for at least the period during which the drainage is desired if removal is deemed traumatic or problematical. The plurality of fibers 12 may have an anticoagulant thereon or there about for resisting the clotting of fluid passing there along and among. The plurality of fibers 12 may include an anti-microbial for deterring the passing of microbes there along and among. The plurality of fibers 12 must be a sterile approved medical grade material for the use described in connection with the apparatus for drainage.

Gathering the external ends 15 of the eight to twelve suture lengths externally can be as shown generally with collector 18 in FIGS. 3, 4, 5, 6, 7, 8, 9, 10, 12, 13, 14, 15 and 16 or with out limitation by shrink tubing, by a molded hub, with adhesive, by friction fit within a piece of tubing, wrapped with tape there about, etc. The particular gathering of external ends 15 should not inhibit fluid flow guided along, among and about the plurality of fibers 12 and the mentioned ways of gathering should accommodate external removal of fluid using pressure differential, gravity, a low or high vacuum. Collector 18 is preferably positioned in fluid communication with gathered together external ends 15 for accumulating bodily fluid guided along, about and among the fibers 12 from internal ends 13 along middle 14 and through the gathered together external ends 15 during drainage of fluid from inside wound or surgical site 11.

Figure 10:
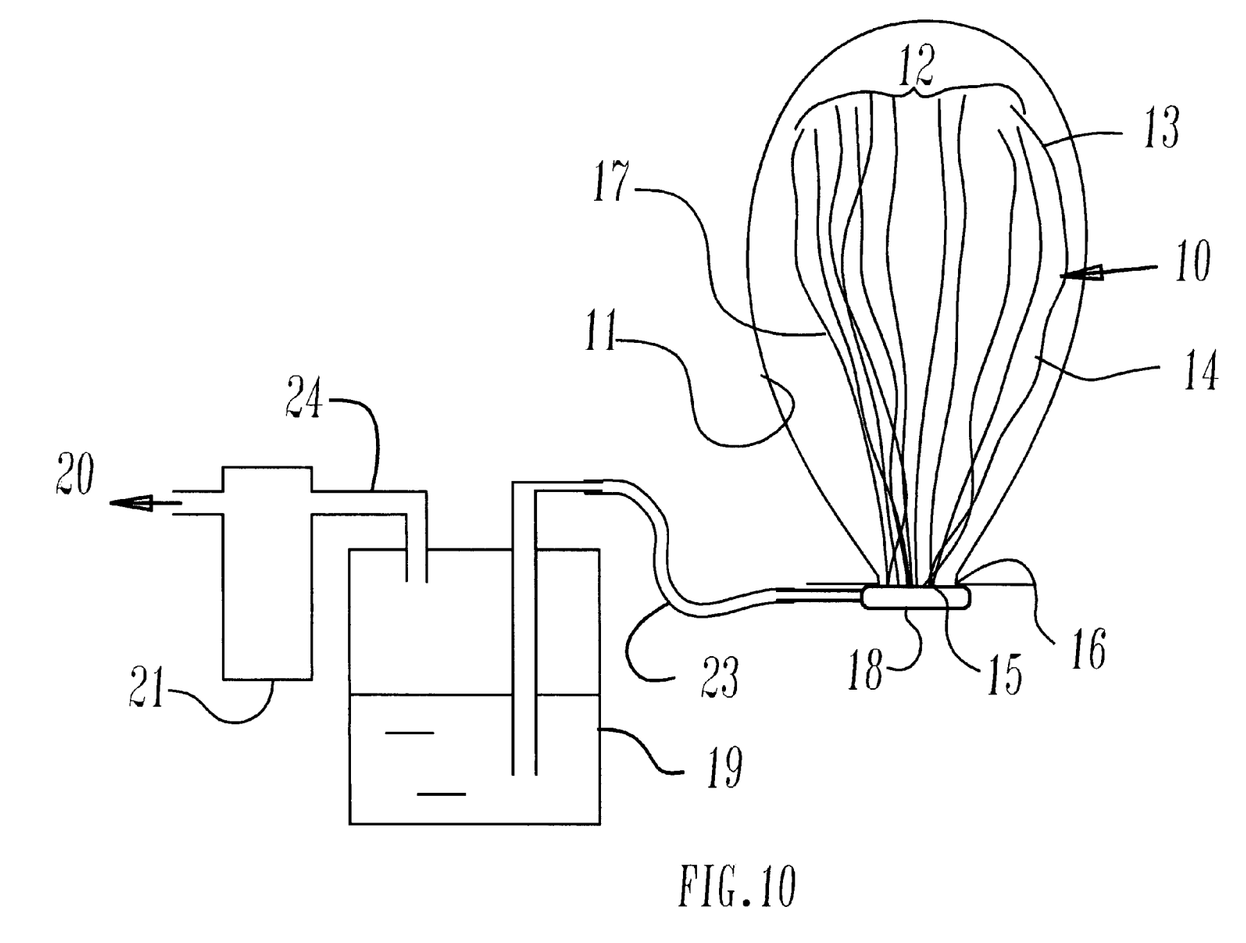
FIG. 10 shows side view in cross section of inside the wound or surgical site with the apparatus for drainage externally connected to an active collector to accept the fluid flowing from the wound or surgical site.
Figure 11:
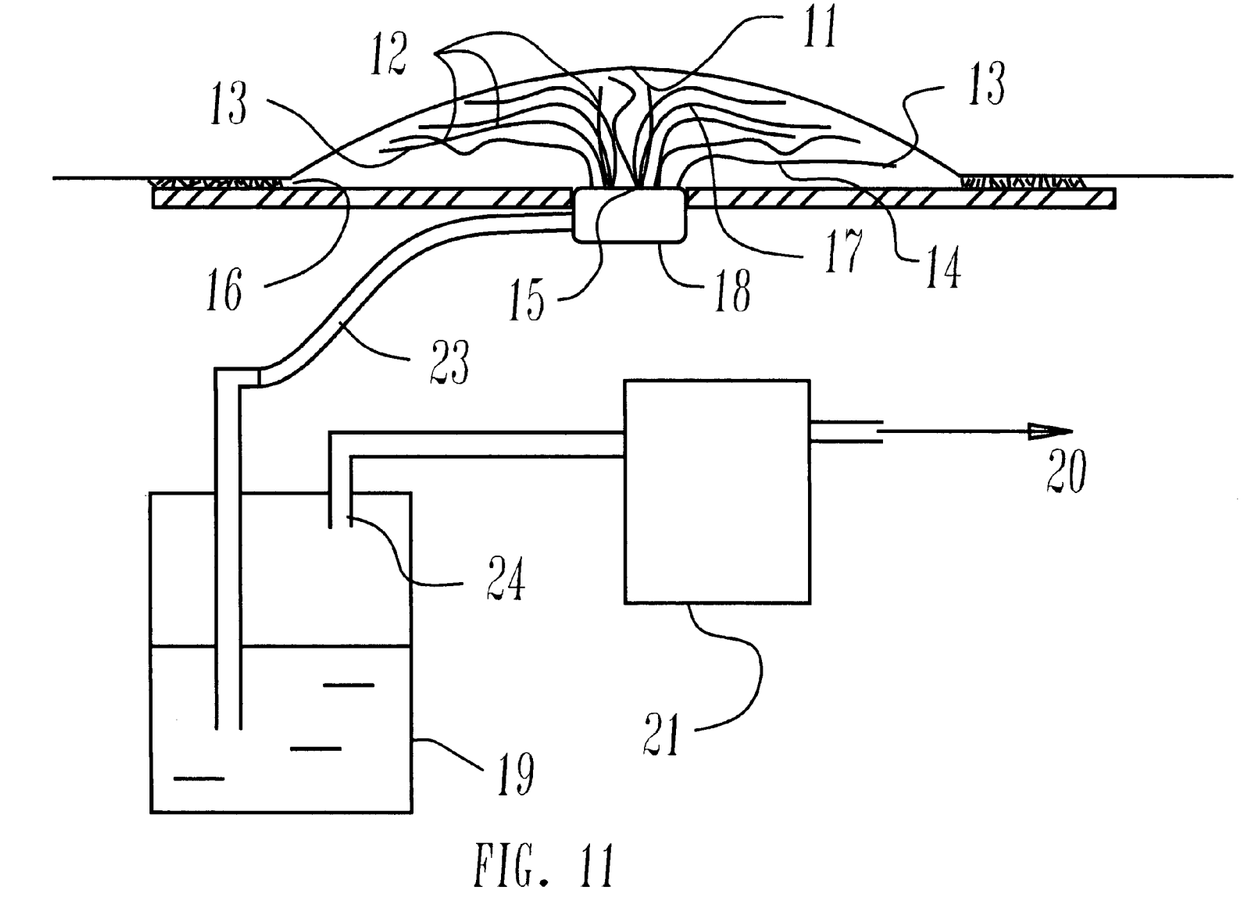
FIG. 11 shows a side view in cross section of the apparatus for drainage applied to a surface wound including a collector that could be held by adhesive or a dressing about the juncture of the collector and the patient's skin.

A canister 19 interposed between source of vacuum 20 and collector 18 in an active closed system accumulates the drained fluid with detritus, as shown in FIGS. 10 and 11. As explained, collector 18 maybe hub shaped and located about gathered together external ends 15 and that would be connected as is common by tubing to source of vacuum 20. Each of the plurality of fibers 12 at their unrestrained internal ends 13 is able to spread divergently inside wound or surgical site 11 to gather the fluids for drainage, for example FIGS. 3, 4, 9, 10, 11, 12 and 14. The internal configuration of the inside of wound or surgical site 11 might take many forms depending on the nature of the particularly surgery and the patient's anatomy thus the apparatus for drainage 10 is of great versatility in that its fiber flexibility easily reaches to accommodate the multitude of different natural features of insides for wound or surgical site 11, see FIGS. 3, 4, 5, 6, 7, 8, 9, 10, 11, 12, 15 and 16. Most importantly, the plurality of fibers 12 at each internal end 13 is free to spread inside wound or surgical site 11 to guide fluids there from along, among and about each fiber 12 through wound or surgical opening 16 to external ends 15 of the plurality of fibers 12. The flexibility and adaptability of the loose bundle 17 formed of plurality of fibers 12 also accommodated the wound or surgical site 11 and opening 16 form or shape that as explained can take many contours. The referenced prior patents and drainage devices do not have the flexibility to spread out within the wound or surgical site or accommodate the cross section of the anatomical opening into the patient's body.

Source of vacuum 20 may connect to draw fluid from collector 18 that is positioned in fluid communication with the gathered together external ends 15, as in FIGS. 10 and 11. In FIGS. 10 and 11, canister 19 is shown located and coupled with tubing between source of vacuum 20 and the collector 18. Hospitals have regulated sources of vacuum 20 with valves mounted in walls and used for drainage. Interposed canister 19 captures the fluid for analysis and safe disposal; see in FIGS. 10 and 11. Source of vacuum 20 may have a regulator 21 connected between it and collector 18 for controlling the amount of vacuum 20 applied to the gathered together external ends 15. Any pressure regulator 21 that permits the adjustment of the amount of vacuum 20 applied can be connected between the source of vacuum 20 and the gathered together external ends 15, again in FIGS. 10 and 11.

It is believed that the guidance of fluid flow from inside wound or surgical site 11 through wound or surgical opening 16 to gathered together external ends 15 may be a result of fluid surface tension, laminar flow or a combination. Fluid passes along and among loose bundle 17 by that or some other way not fully understood. This is to be distinguished from the flow within drain tubes that is through an internal passageway or through channels. Loose bundle 17 of fibers 12 provides paths along, about, among or through each of fibers 12 that guide fluid draining from inside wound or surgical site 11 somewhat as water is know to follow or flow along a string, wire, rod, or like surface, etc. Surface tension is recognized as the attractive force exerted upon the surface molecules of a liquid by the molecules beneath that tend to draw the surface molecules into the bulk of the liquid and make the liquid assume a shape having the least surface area. It is thought that fluid draining from inside wound or surgical site 11 may exhibit those attractive forces that minimize surface area of the liquid molecules and cause the fluid flow to follow along, among and about each of the plurality of fibers 12. The fluid coagulation seems to be less of a problem perhaps because the flexibility, shape and surface area of loose bundle 17 of fibers 12 is less conducive to coagulating than inside tubing or channels. That is not to say that this is only or exactly what happens but to suggest an explanation of why fluid is guided along, about, among and through loose bundle 17. Significantly, the spaces along and around each fiber 12 seem to allow the fluid to flow with greater freedom than through the internal passageway of a tubular drain or channels with or without wicks.

It can thus be appreciated that although coagulation may be less of a problem with the plurality of fibers 12 than tubular drains or channels. Loose bundle 17 easily provides guidance of fluid flow from throughout the inside of wound or surgical site 11 through wound or surgical opening 16 and to the gathered external ends 15. The freedom of movement that allows spreading, shifting and ultimately contraction of the fibers 12 of loose bundle 17 seems to help healing by guiding fluid flow, resisting coagulation and minimizing traumatic percutaneous passage. Perhaps it is the ability of the individually flexible fibers 12 to move somewhat especially in the middle 14 and internal ends 13 relative to one another. Specifically, at least at their internal ends 13 the plurality of fibers 12 spread while middle 14 shifts accommodating the cross sectional shape of wound or surgical opening 16 gives this result. Tubular drains including those having outside channels as disclosed in the background cannot spread out within the wound or surgical site 11. Although filament is preferred the advantages of spreading divergently each of the fibers 12 in loose bundle 17 remains no matter what type of material is used for each individual fiber 12.

A method for draining the inside of a wound or surgical site 11 of a human or animal uses the apparatus for drainage 10 and includes steps of providing a plurality of fibers 12 each flexible and having an internal end 13, an external end 15 and a middle 14 there between, each fiber 12 is independent and elongate with a thickness and a length wherein its thickness is substantially less than its length for flexibility. The fibers freely spread within the wound or surgical site 11 but the step of holding the plurality of fibers 12 together near the gathered external ends 15 allows collection for drainage. The step of allowing the internal ends 13 to remain unrestrained for spreading out is performed.

Figure 13:
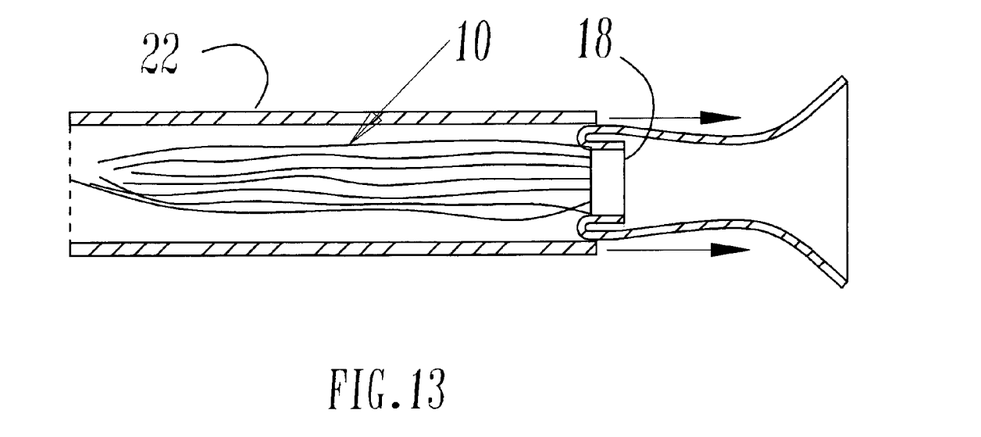
FIG. 13 shows in cross section the introducer over the apparatus for drainage as used during placement of the apparatus for drainage.

Although not essential it has been found to aid in the step of delivering of the plurality of fibers 12 the step of placing them while they are within a tubular introducer 22, as shown in FIG. 13. Thus, the enclosed fibers 12 in loose bundle 17 are contained in introducer during introduction so they may be inserted through wound or surgical opening 16 and placed inside the wound or surgical site 11. Withdrawal of introducer 22, see FIGS. 13 and 15 over the gathered together external ends 15 and the collector 18 allows internal ends 13 to expand spreading or fanning out inside the wound or surgical site 11. Tubular introducer 22 is internally large enough to be easily drawn out of wound or surgical opening 16 over the gathered together external ends 15 and collector 18 while leaving apparatus for drainage 10 in place inside wound or surgical site 11 and through wound or surgical opening 16.

Figure 12:
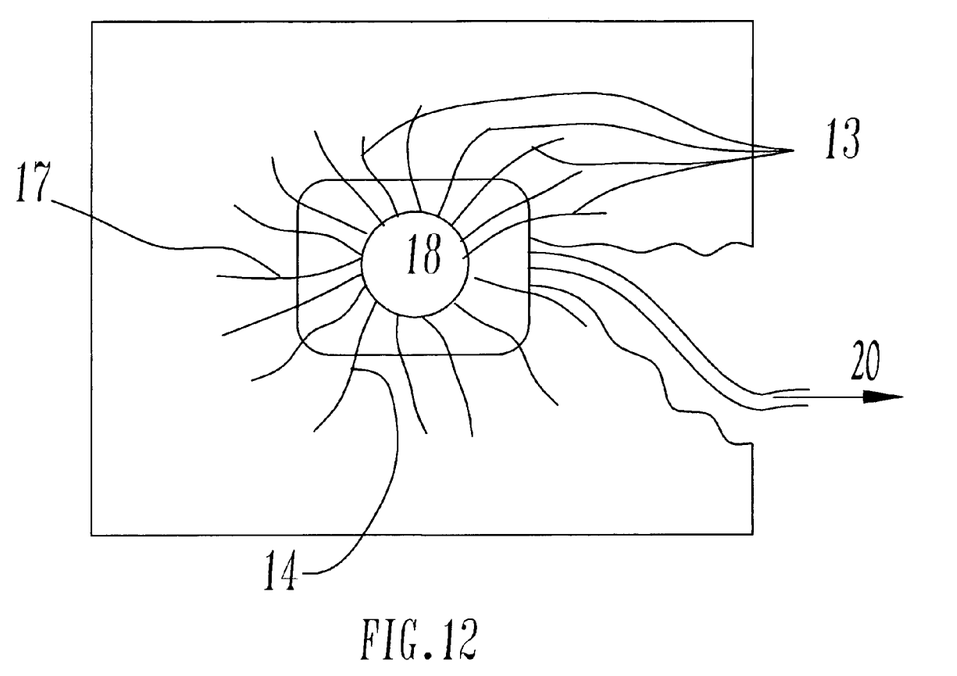
FIG. 12 shows a plan view of the apparatus for drainage of FIG. 11 shown from the side applied to a surface wound held by the adhesive dressing and including an active collector system in fluid communication with the external ends of the gathered together bundle.
Figure 14:
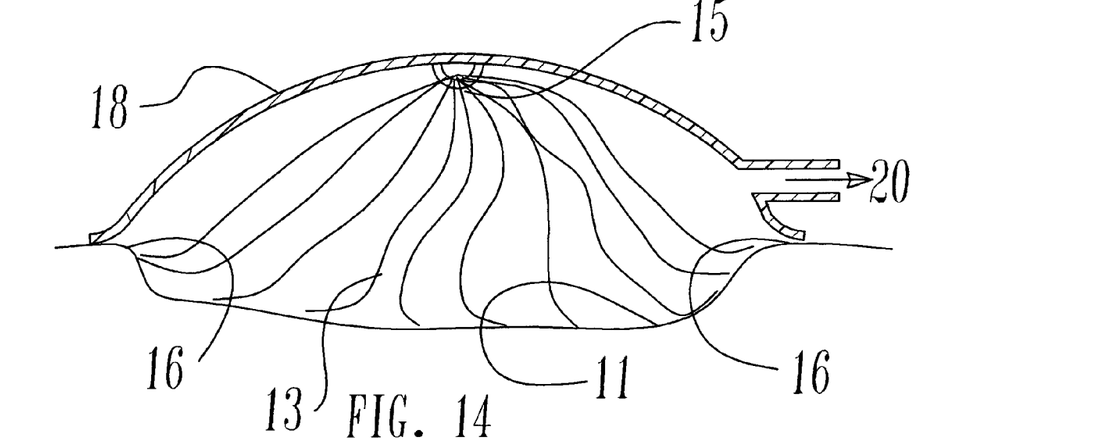
FIG. 14 shows in cross section the apparatus for drainage over a wound opening with the plurality of fibers spread through out the wound.
Figure 15:
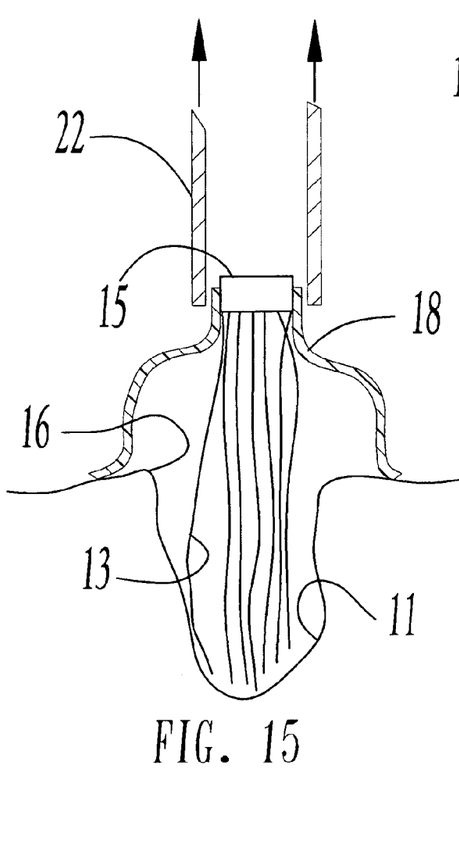
FIG. 15 shows in cross section the apparatus for drainage after placement and with the introducer shown being removed.
Figure 16:
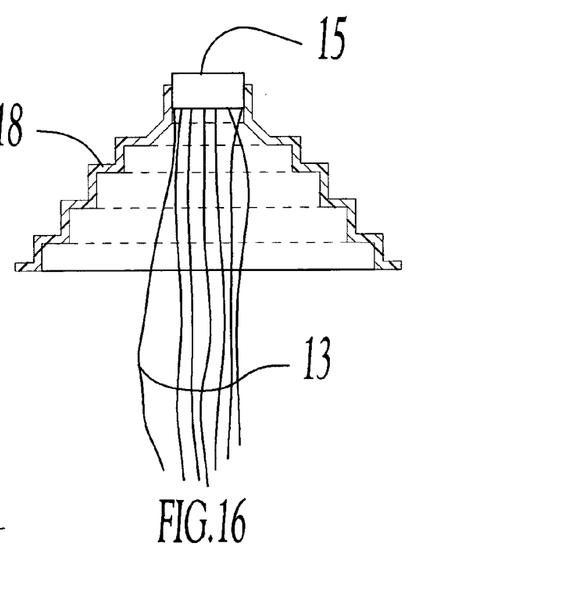
FIG. 16 shows in cross section the apparatus for drainage with a bellows shaped collector that is flexible for accommodating the wound opening size.

The flexibility of the plurality of fibers 12 allows each of the internal ends 13 to independently spread or fan throughout the wound or surgical site 11. Positioning collector 18 in fluid communication with gathered together external ends 15 is a step to accumulate drained fluid. As can be appreciated gathered together external ends 15 are in fluid communication with collector 18 so accumulated the fluid may be captured. The preferred approach is to have collector 18 receive in conjugating mating engagement with gathered together external ends 15. The step of guiding bodily fluid along, about and amongst the fibers 12 from the internal ends 13 along middle 14 and to gathered together external ends 15 during drainage of fluid from inside wound or surgical site 11 is preferred. As explained it is believed to be a result of surface tension that guides the fluid along and among fibers 12 and out of the body. The plurality of fibers 12 at their unrestrained internal ends 13 are located inside wound or surgical site 11 for the step of spreading divergently for accumulating bodily fluid and for guiding bodily fluid along, about and amongst the fibers 12 from internal ends 13 along middle 14 and to gathered together external ends 15 during drainage. There appears to be no ideal angle or curve of the fibers 12 to facilitate the step of guiding the fluid from the wound or surgical site 11. The time required for drainage is a function of the nature healing of the surgery, trauma or wound. The advantage of the apparatus for drainage 10 would seem to be the accumulation of fluid from throughout the inside of wound or surgical site 11 while minimizing coagulation. FIGS. 11 and 14 show a side view in cross section of the apparatus for drainage applied to the surface wound including a collector held by an adhesive dressing about the external ends of the gathered together bundle. Note that the wound opening 16 is greater than the depth of the wound site 11 allowing the fibers 12 to spread out. FIG. 12 shows a bottom plan view of the apparatus for drainage of FIG. 11 shown from the side applied about the surface wound including an active collector system about the external ends of the gathered together bundle held by the adhesive dressing. FIGS. 13 and 15 show in cross section the introducer 22 fit over the apparatus for drainage as used during placement of the apparatus for drainage 10. FIG. 14 shows in cross section the apparatus for drainage over a wound opening with the plurality of fibers spread through out the wound. The collector 18 is a shallow bell shape and can be altered in size to accommodate different wound shapes, FIGS. 14 and 15. The gathered together ends 15 are wrapped about a loop inside the top of the collector 18 in FIG. 14 and the source of vacuum 20 draws off fluids collected. FIG. 15 shows in cross section the step of apparatus for drainage 10 after placement with introducer 22 being removed over the gathered together external ends 15 and collector 18. This removal is similar to that shown in FIG. 13 except in FIG. 13 the apparatus for drainage 10 is flipped inside out to assist introduction into a deep surgical site 11 yet still permit handling by the inverted collector 18 during removal of the introducer 22. FIG. 16 shows in cross section the apparatus for drainage 10 with a bellows shaped collector 18 which can be collapsed or inverted during placement.

For active drainage collector 18 can be used with canister 19. An inlet 23 receives or connects with collector 18 and gathered together external ends 15 so that when suction is applied to canister 19 the fluid passes into canister 19 and is trapped therein because the suction is applied at the surface of the accumulated fluid via outlet 24, as best depicted in FIGS. 10 and 11. For passive accumulation gathered together external ends 15 are connected to collector 18 and pressure differential, gravity or absorbent media can be used to draw or move the fluid into collector 18. A typical bulb 25 evacuates the fluid by the pressure differential between the inside of the collapsed bulb 25 and inside of the wound or surgical site 11 see FIG. 9. The bulb 25 expands to its normal shape drawing fluid from collector 18 into the bulb 25. The method also has the step of connecting a source of vacuum 20 and actively drawing fluid from collector 18 positioned in fluid communication with gathered together external ends 15. The step of controlling the source of vacuum 20 with regulator 21 connected between source of vacuum 20 and collector 18 is sometimes desirable. Adjustment can be made by bleeding off some of the suction to reduce fluid flow as needed.

Also in the method it is preferred that the step of selecting flexible fibers 12 from the group consisting essentially of filaments, strings, strands, hollow fibers or any combination thereof or made from a biocompatible material selected from the group consisting essentially of polymers, cellulose, natural substances or any combination thereof. The step of using biocompatible material being bio-absorbable is desired. The length of time before the fibers 12 are absorbed should be commensurate with the length of time needed for healing or drainage. The gathered external ends 15 being outside the body will most probably last longer and can be simply removed from wound or surgical opening 16 by pulling outwardly on the collector or gathered external ends 15. The step of including an anticoagulant for resisting the clotting of fluid passing along the plurality of fibers 12 is valuable as is the step of including an anti-microbial for deterring the passing of microbes along the plurality of fibers 12. Anti-microbial materials are well known and include any of the bactericides, silver compounds, etc. Alloying, filling or otherwise adding such active ingredients to flexible fibers are steps common in connection with medical tubing.

The step of introducing the plurality of fibers 12 within the introducer 22 by the step of constraining at least internal ends 13 and middle 14 with introducer 22 and the step of removing introducer 22 while leaving the plurality of fibers 12 inside wound or surgical site 11 is preferred and thus the step of spreading divergently internal ends 13 results inside wound or surgical site 11.

Figure 5:
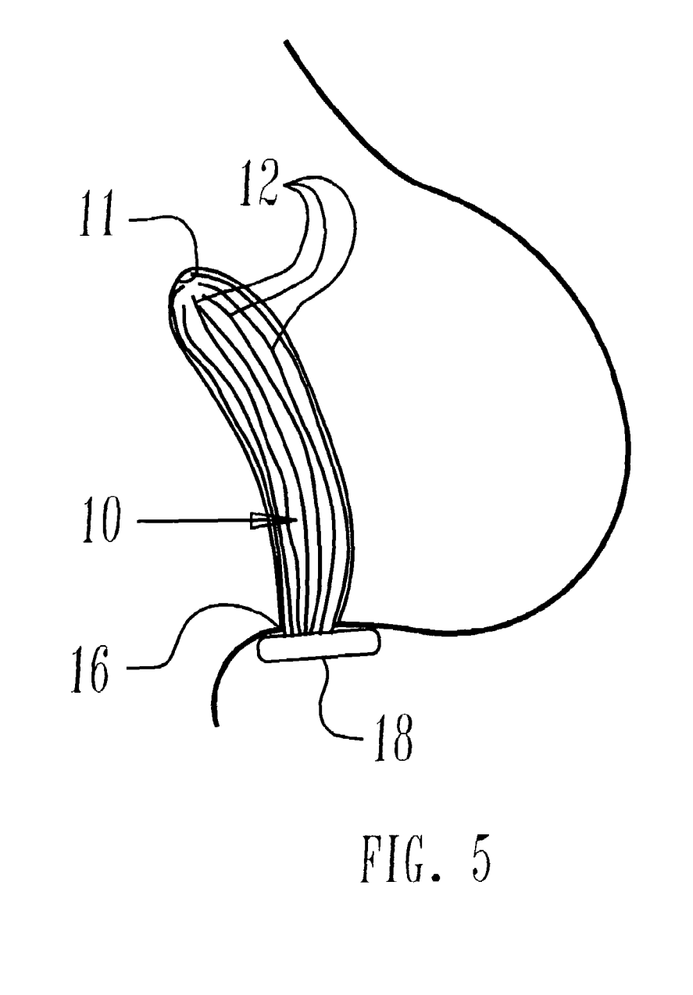
FIG. 5 is a side view of the apparatus for drainage placed in the wound or surgical site shown in cross section and wherein the internal ends of the loose bundle of fibers have contracted as the wound or surgical site cavity heals.
Figure 6:
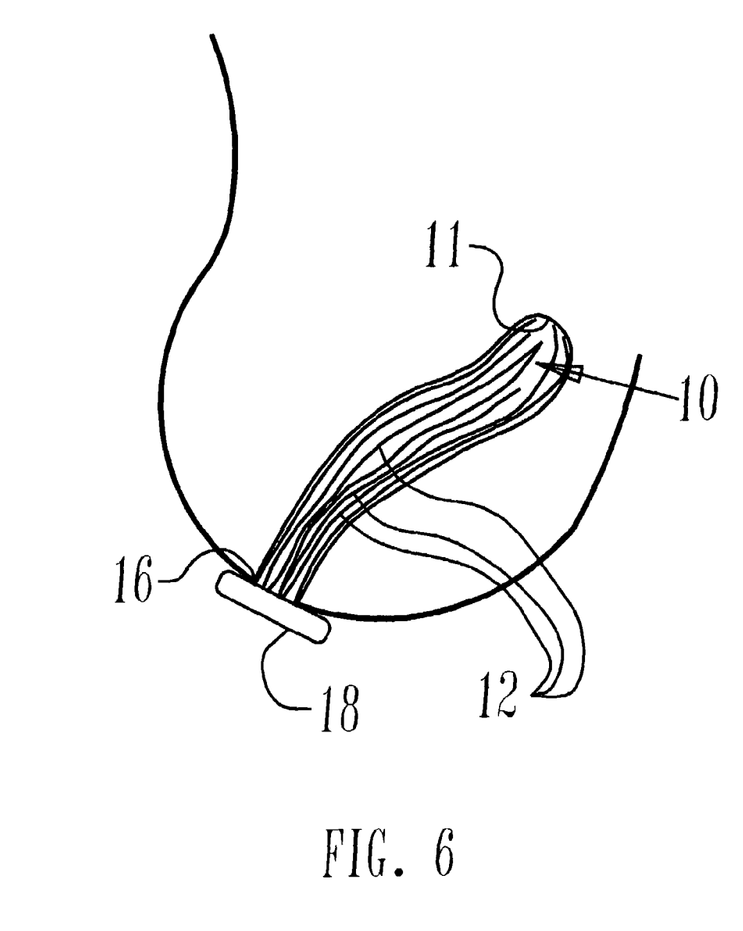
FIG. 6 is a front view of the apparatus for drainage placed in the wound or surgical site shown in cross section and wherein the internal ends of the loose bundle of fibers have contracted as the wound or surgical site cavity heals.
Figure 7:
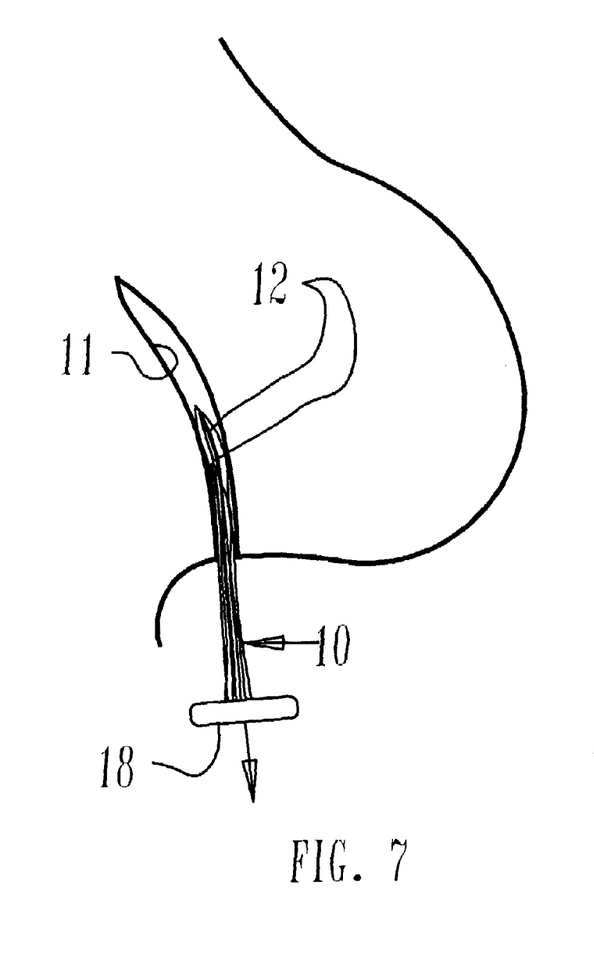
FIG. 7 is a side view of an apparatus for drainage as it is removed from a wound or surgical site shown in cross section and wherein the internal ends of the loose bundle of fibers have come together easing their removal.
Figure 8:
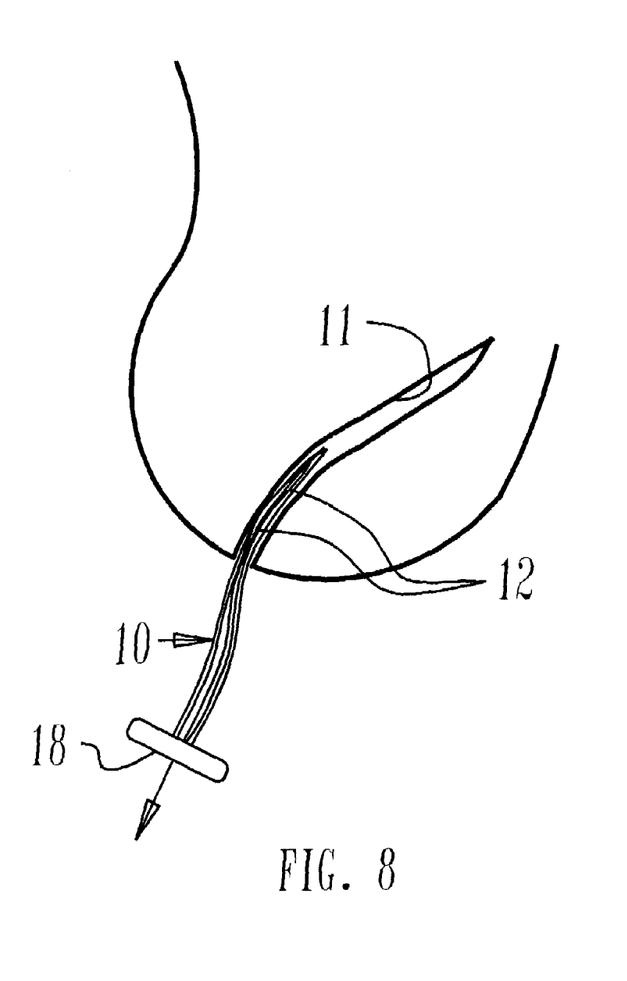
FIG. 8 is a front view of the apparatus for drainage as it is removed from the wound or surgical site shown in cross section and wherein the internal ends of the loose bundle of fibers have come together easing their removal.
Figure 9:
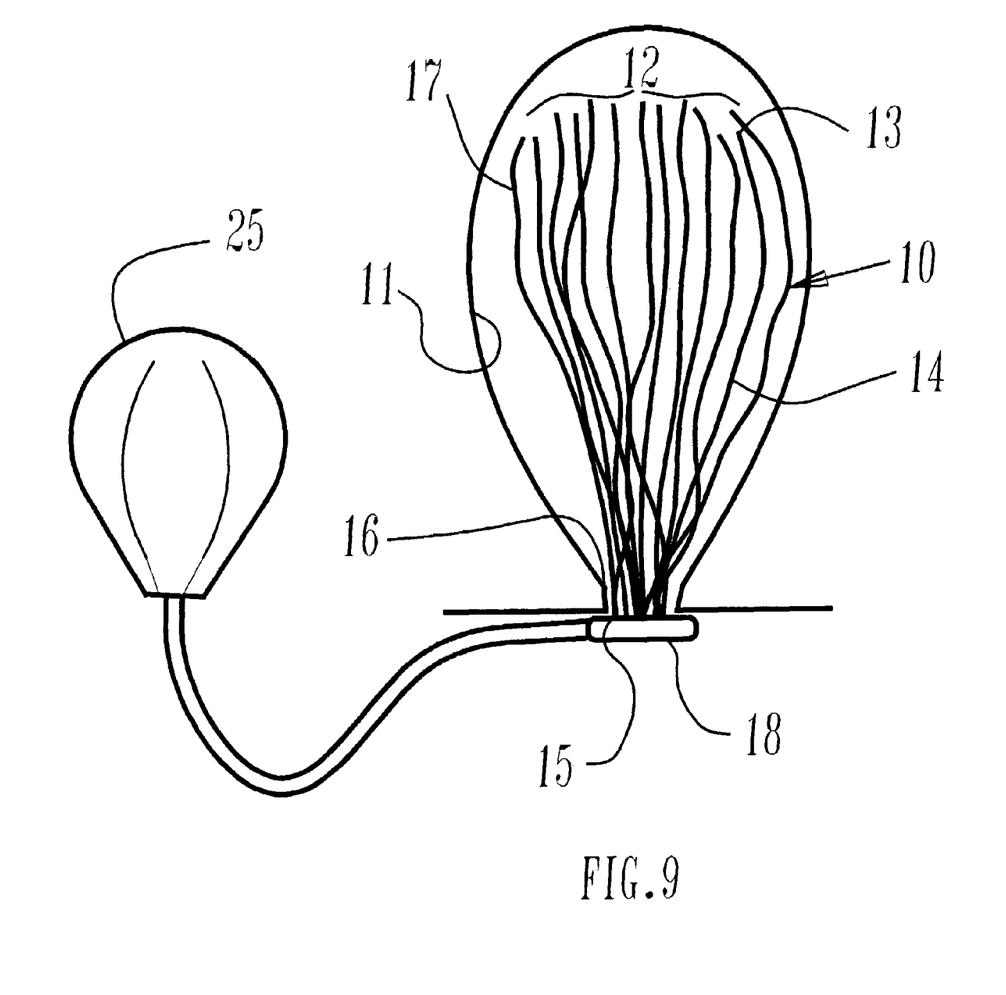
FIG. 9 shows a cross sectional view of inside the wound or surgical site with the apparatus for drainage externally connected to a passive collector to accept the fluid flowing from inside the wound or surgical site.

The step of allowing the plurality of fibers 12 in middle 14 to shift relative to one another so that the cross section thereof may approximate the cross section of a percutaneous incision of surgical opening 16 through which middle 14 passes for guiding drainage during healing is preferred. The different cross sections of wound or surgical openings 16 are a function of how each is made typically a surgical incision is linear, a trocar opening is a rough tear or puncture but a wound can be almost any shape or depth. Middle 14 of each fiber 12 of the loose bundle 17 is able to shift relative to any other fiber or fibers 12 to accommodate the cross section of the wound or surgical openings 16 through which it passes and remains during healing. That is to say that the healing process would cause wound or surgical opening 16 to decrease in cross section as seen in FIGS. 5 and 6 and normally wound healing tends to be flexible in cross section as it progresses.

A method of manufacture of an apparatus for drainage 10 that fits anatomically humans or animals within a wound or surgical site 11 has steps. The apparatus for drainage 10 passing from inside wound or surgical site 11 percutaneously and extending externally for accumulation of fluids. The steps of manufacture include accumulating a plurality of fibers 12 each with an internal end 13, an external end 15 and a middle 14 there between in a loose bundle 17 and gathering together each fiber 12 elongate with a thickness and a length wherein its thickness is substantially less than its length for flexibility at their gathered external ends 15 while leaving internal ends 13 unrestrained. It is preferred during manufacture to position collector 18 in fluid communication with gathered together external ends 15 for accumulating bodily fluid guided along and amongst the fibers 12 from internal ends 13 along middle 14 and to gathered together external ends 15 during drainage of fluid from inside wound or surgical site 11.

During manufacture the step of gathering together external ends 15 can be accomplished, for example, wrapping with tape, fitting within tubing that can be heated and shrunk, containing within a hub or holding together with adhesive placed to allow fluid flow to pass. With respect to manufacture by adhesive holding, one way would be, for example, to peripherally join the external ends 15 of fibers 12 so that passage of fluid can take place within, about, along, among and through loose bundle 17 and into collector 18. That is to say that the adhesive would essentially be peripherally surrounding gathered external ends 15 but would not restrain flow along, about, within and among fibers 12 in loose bundle 17.

Although the apparatus for drainage 10 and methods of use and manufacturing herein have been described with reference to particular embodiments, methods and illustrations, it is to be understood that these embodiments merely show the principles and applications of the presently preferred apparatus and methods. It is therefore to be understood that numerous modifications may be made to the described and illustrated embodiments and that other arrangements and materials may be devised without departing from the spirit and scope of the present invention as defined by the appended claims. The plurality of fibers 12 are flexible and in a loose bundle 17 thus free to spread and move within the wound or surgical site permitting collection and guiding of the drainage from the internal ends along, among and about one or all of the plurality of fibers 12 to the collector 18.

What is claimed is:

1. An apparatus for drainage of a wound or surgical site and anatomical opening of a human or animal fits anatomically and passes from inside the wound or surgical site and anatomical opening percutaneously and extends externally for accumulation of fluids, the apparatus for drainage comprises:

a plurality of fibers each having an internal end, an external end and a middle there between, each fiber elongate with a thickness and a length wherein its thickness is substantially less than its length for flexibility, the plurality of fibers having gathered together external ends leaving the internal ends unrestrained to spread in the wound or surgical site and anatomical opening;

an external collector cover positioned in fluid communication with the gathered together external ends for accumulating bodily fluid guided along and amongst the one or more of the plurality of fibers without any supporting sheath or tubing extending thereabout or surrounding the plurality of fibers from the internal ends along the middle and to the gathered together external ends during drainage of fluid from inside and percutaneously through the wound or surgical site and anatomical opening, and the plurality of fibers flexible so that at their unrestrained internal ends each fiber is able to spread divergently of the other fibers while inside and percutaneously through the wound or surgical site and anatomical opening to anatomically fit percutaneously in or through the wound or surgical site and anatomical opening for drawing and guiding fluid from inside the wound or surgical site and anatomical opening to the gathered together external ends during drainage.

2. The apparatus of claim 1 with a source of vacuum in fluid communication with and connected to actively draw fluid from the external collector cover positioned over and in fluid communication with the gathered together external ends and over the wound or surgical site and anatomical opening.

3. The apparatus of claim 1 with each of the plurality of the fibers selected from the group consisting essentially of filaments, strings, strands, hollow fibers or any combination thereof.

4. The apparatus of claim 1 with the plurality of fibers made from a biocompatible material selected from the group consisting essentially of polymers, cellulose, natural substances or any combination thereof.

5. The apparatus of claim 4 with the biocompatible material being bio-absorbable.

6. The apparatus of claim 1 with the plurality of fibers including an anticoagulant for resisting the clotting of fluid passing there along, about and among.

7. The apparatus of claim 1 with the plurality of fibers including an anti-microbial for deterring the passing of microbes there along, about and among.

8. The apparatus of claim 2 with the source of vacuum being less than atmospheric and with a regulator connected between the source of vacuum and the external collector cover to control the amount of vacuum applied to the gathered together external ends.

9. A method for drainage of a wound or surgical site of a human or animal, the method includes apparatus that fits anatomically and passes from inside the wound or surgical site percutaneously and extends externally for accumulation of fluids, the method for drainage including the steps of:

providing a plurality of fibers each having an internal end, an external end and a middle there between, each fiber elongate with a thickness and a length wherein its thickness is substantially less than its length for flexibility;

gathering the plurality of fibers together near their external ends;

allowing the internal ends and middle to remain unrestrained for spreading within the wound or surgical site and anatomical opening; guiding bodily fluid along and amongst the fibers from the internal ends along the middle and percutaneously without any supporting sheath or tubing extending thereabout or surrounding the plurality of fibers and to the gathered together external ends during drainage of fluid from a wound or surgical site and anatomical opening;

positioning an external collector cover over and in fluid communication with the gathered together external ends and covering the wound or surgical site and anatomical opening;

accumulating bodily fluid in the external collector cover from plurality of fibers at their unrestrained internal ends which are inside the wound or surgical site and anatomical opening, and spreading divergently at least the internal ends for accumulating bodily fluid and for guiding bodily fluid along and amongst the fibers from the internal ends along the middle and percutaneously without any supporting sheath or tubing extending thereabout or surrounding the plurality of fibers and to anatomically fit percutaneously in or through the wound or surgical opening for drawing and guiding fluid from inside the wound or surgical site and anatomical opening to the gathered together external ends during drainage.

10. The method of claim 9 with the steps of connecting in fluid communication a source of vacuum to the external collector cover and actively drawing fluid from the external collector cover, and actively drawing fluid from the external collector cover positioned over and in fluid communication with the gathered together external ends.

11. The method of claim 9 with the step of using flexible fibers for draining by selecting the plurality of fibers from the group consisting essentially of filaments, strings, strands, hollow fibers or any combination thereof for use in draining.

12. The method of claim 9 with the step of using flexible fibers made from a biocompatible material selected from the group consisting essentially of polymers, cellulose, natural substances or any combination thereof for draining.

13. The method of claim 12 with the step of using biocompatible material being bio-absorbable during the period of draining for the plurality of fibers.

14. The method of claim 9 with the step of including an anticoagulant on the plurality of fibers for resisting the clotting of fluid passing along, among and about the plurality of fibers during draining.

15. The method of claim 9 with the step of including an anti-microbial on the plurality of fibers for deterring the passing of microbes along, among and about the plurality of fibers during draining.

16. The method of claim 10 with the step of controlling the source of vacuum with a regulator connected between the source of vacuum and the external collector cover for adjusting vacuum applied during draining.

17. The method of claim 9 with the step of introducing the plurality of fibers by the steps of constraining at least the internal ends and the middle with an introducer during only the insertion of the plurality of fibers, and removing the introducer while leaving at least the internal ends of the plurality of fibers inside the wound or surgical site for guiding drainage percutaneously without any supporting sheath or tubing extending there about or surrounding the plurality of fibers to anatomically fit percutaneously in or through the wound or surgical site and anatomical opening for drawing and guiding fluid from inside the wound or surgical site and anatomical opening to the gathered together external ends during drainage.

18. The method of claims 17 with the step of spreading divergently the internal ends inside the wound or surgical site.

19. The method of claim 17 with the step of holding the external collector during placement of the plurality of fibers within the introducer in the wound or surgical site and anatomical opening.

20. The method of claim 17 with the step of allowing the plurality of fibers in the middle to flex and shift relative to one another so that the cross section thereof approximates the cross section of the surgical site percutaneous incision through which the middle passes percutaneously without any supporting sheath or tubing extending or thereabout or surrounding the plurality of fibers for guiding drainage during healing.

21. A method of manufacture of an apparatus for drainage of a wound or surgical site and anatomical opening of a human or animal so the apparatus fits anatomically and passes from inside the wound or surgical site and anatomical opening percutaneously and extends externally for accumulation of fluids, the method for manufacture having the steps of:

accumulating a plurality of fibers each having an internal end, an external end and a middle there between in a loose bundle; gathering together each fiber elongate with a thickness and a length wherein its thickness is substantially less than its length for flexibility at their external ends while leaving the internal ends unrestrained, and     positioning an external collector cover over and in fluid communication with the gathered together external ends for accumulating bodily fluid guided along, about and amongst the fibers from the internal ends along the middle percutaneously without any supporting sheath or tubing extending thereabout or surrounding the plurality of fibers and to anatomically fit percutaneously in or through the wound or surgical site and anatomical opening for drawing and guiding fluid from inside the wound or surgical site and anatomical opening to the gathered together external ends during drainage of fluid from inside the wound or surgical site and anatomical opening.

22. The method of claim 21 with the step of assembling the apparatus for drainage movably within an introducer during only the insertion of the plurality of fibers and for removal of the introducer after insertion.

\* \* \* \* \*